(12) United States Patent
Keller et al.

(10) Patent No.: US 6,503,195 B1
(45) Date of Patent: Jan. 7, 2003

(54) METHODS AND SYSTEMS FOR REAL-TIME STRUCTURED LIGHT DEPTH EXTRACTION AND ENDOSCOPE USING REAL-TIME STRUCTURED LIGHT DEPTH EXTRACTION

(75) Inventors: Kurtis P. Keller, Chapel Hill, NC (US); Jeremy D. Ackerman, Chapel Hill, NC (US); Michael H. Rosenthal, Chapel Hill, NC (US); Henry Fuchs, Chapel Hill, NC (US); Andrei State, Chapel Hill, NC (US)

(73) Assignee: University of North Carolina at Chapel Hill, Chapel Hill, NC (US)

(*) Notice: Subject to any disclaimer, the term of this patent is extended or adjusted under 35 U.S.C. 154(b) by 0 days.

(21) Appl. No.: 09/317,932

(22) Filed: May 24, 1999

(51) Int. Cl.[7] .................................................. A61B 1/04
(52) U.S. Cl. ...................... 600/160; 600/109; 600/111; 600/166; 348/45
(58) Field of Search ................................ 600/109, 111, 600/117, 160, 166, 181; 348/45, 65

(56) References Cited

U.S. PATENT DOCUMENTS

| | | | |
|---|---|---|---|
| 5,109,276 A | * | 4/1992 | Nudelman et al. ............ 348/45 |
| 5,323,002 A | | 6/1994 | Sampbell et al. |
| 5,371,543 A | | 12/1994 | Anderson |
| 5,446,798 A | | 8/1995 | Morita et al. |
| 5,452,024 A | | 9/1995 | Sampsell |
| 5,457,493 A | | 10/1995 | Leddy et al. |
| 5,488,431 A | | 1/1996 | Gove et al. |
| 5,489,952 A | | 2/1996 | Gove et al. |
| 5,491,510 A | | 2/1996 | Gove |
| 5,526,051 A | | 6/1996 | Gove et al. |
| 5,532,997 A | | 7/1996 | Pauli |
| 5,541,723 A | | 7/1996 | Tanaka |
| 5,570,135 A | | 10/1996 | Gove et al. |
| 5,608,468 A | | 3/1997 | Gove et al. |
| 5,612,753 A | | 3/1997 | Poradish et al. |
| 5,629,794 A | | 5/1997 | Magel et al. |
| 5,630,027 A | | 5/1997 | Venkateswar et al. |
| 5,699,444 A | | 12/1997 | Palm |
| 5,870,136 A | | 2/1999 | Fuchs et al. |

OTHER PUBLICATIONS

Zitnick et al., "Multi–Base Stereo Using Surface Extraction," Visual Interface Inc., (Nov. 24, 1996).

Bajura et al., "Merging Virtual Objects with the Real World: Seeing Ultrasound Imagery within the Patient," Proceedings of SIGGRAPH 92, vol. 2 (No. 26), pp. 203–210, (Jul. 20,1992).

Ohbuchi et al., "Incremental Volume Reconstruction and Rendering for 3D Ultrasound Imaging," Visualization in Biomedical Computing, SPIE Proceedings, pp. 312–323, (Oct. 13, 1992).

State et al., "Superior Augmented Reality Registration by Integrating Landmark Tracking and Magnetic Tracking," Computer Graphics Proceedings, Proceedings of SIGGRAPH 96—Annual Conference Series (New Orleans, Louisiana), pp. 429–438, (Aug. 4, 1996).

(List continued on next page.)

*Primary Examiner*—John Mulcahy
(74) *Attorney, Agent, or Firm*—Jenkins & Wilson, P.A.

(57) ABSTRACT

A real-time structured light depth extraction system includes a projector for projecting structured light patterns onto an object of interest. A camera positioned off-axis from the projector samples light reflected from the object synchronously with the projection of structured light patterns and outputs digital signals indicative of the reflected light. An image processor/controller receives the digital signals from the camera and processes the digital signals to extract depth information of the object in real time.

15 Claims, 11 Drawing Sheets

(1 of 11 Drawing Sheet(s) Filed in Color)

OTHER PUBLICATIONS

State et al., "Technologies for Augmented Reality Systems," Computer Graphics Proceedings, Proceedings of SIGGRAPH 96, Annual Conference Series (New Orleans, Louisiana), pp. 439–446, (Aug. 4, 1996).

Garrett et al., "Real–Time Incremental Visualization of Dynamic Ultrasound Volumes Using Parallel BSP Trees," Proceedings of IEEE Visualization of Dynamic Ultrasound Volumes Using Parallel BSP Trees, pp. 235–240, (Oct. 27, 1996).

Jacobs et al., "Managing Latency in Complex Augmented Reality Systems," Proceedings of 1997 Symposium on Interactive 3D Graphics, Annual Conference Series, ACM SIGGRAPH (Providence, Rhode Island), pp. 49–54, (Apr. 27, 1997).

Livingston et al., "Magnetic Tracker Calibration for Improved Augmented Reality Registration," Presence: Teleoperators and Virtual Environments, MIT Press, vol. 6 (No. 5), pp. 532–546, (Oct. 21, 1997).

Advertisement, "Virtuoso," Visual Interface, Inc., Visual Interface, Inc. (www.visint.com), (Dec. 21, 1998).

Advertisement, "Virtuoso," Visual Interface, Inc., (1998).

Advertisement, "Inspeck 3DC 3D Capturor," Inspeck 3DC 3D Capturor (www.inspeck.com) (1998).

Advertisement, "Virtual 3D High Speed Non–Contact Surface Perception," Virtual 3–D Technologies Corporation (www.virtual3dtech.com), (Dec. 21, 1998).

Ohbuchi, "Incremental Acquisition and Visualization of 3D Ultrasound Images", Ph.D. Dissertation, UNC–CH Computer Science Technical Report TR95–023, (1993).

Ohbuchi et al. "An Incremental Volume Rendering Algorithm for Interactive 3D Ultrasound Imaging", UNC–CH Computer Science Technical Report TR91–023, (1991).

Fuchs et al. "Towards Performing Ultrasound–Guided Needle Biopsies from Within a Head–Mounted Display", 4th International Conference, VBC '96, Hamburg, Germany, (Sep. 22–25, 1996).

Depiero et al., "3–D Computer Vision Using Structured Light: Design, Calibration and Implementation Issues," The University of Tennessee, pp. 1–46, (1996).

Fuchs et al., "Augmented Reality Visualization for Laparoscopic Surgery," MICCAI, vol. 11 (No. 13), pp. 934–943, (Oct. 1998).

State et al., "Case Study: Observing a Volume Rendered Fetus within a Pregnant Patient," IEEE Visualization Conference, 5th ed., pp. 364–368, (1994).

* cited by examiner

METHODS AND SYSTEMS FOR REAL-TIME STRUCTURED LIGHT DEPTH EXTRACTION AND ENDOSCOPE USING REAL-TIME STRUCTURED LIGHT DEPTH EXTRACTION

GOVERNMENT INTEREST

This invention was made with government support under grant number DABT63-93-C-0048 from the Advanced Research Projects Agency (ARPA) and under grant number 8920219 from the National Science Foundation. The Government has certain rights to this invention.

TECHNICAL FIELD

The present invention relates to methods and systems for determining depth information relating to a scene so that a three-dimensional image of the scene can be displayed on a display device. More particularly, the present invention relates to methods and systems for real-time structured light depth extraction and an endoscope using real-time structured light depth extraction.

BACKGROUND ART

In computer imaging systems, it is often desirable to determine depth information relating to an object or scene so that a three-dimensional image of the object can be displayed on a display device. One method for determining depth information is stereo depth extraction. In stereo depth extraction, two or more cameras are utilized to view an object. Determining the distance of the object from the cameras requires that both cameras focus on the same feature. This method is useful in determining depth of uncomplicated objects where all corners and edges of an object are well pronounced in a scene. However, curved edges, shading, non-planar surfaces, and uneven lighting make stereo depth extraction difficult because these conditions may prevent identification of a common feature that both cameras can resolve.

Another conventional method for extracting depth information from a scene is laser scanned depth extraction. In laser scanned depth extraction, a laser line is projected across a surface and viewed off-axis using a camera. Provided that the locations of the laser and the camera are known, scanning the laser line across the surface of the object allows a computer to build a three-dimensional depth model of the object. One disadvantage associated with laser scanned depth extraction is that the time for scanning a laser across the entire surface of an object makes this method impractical for real-time depth extraction systems.

In order to increase the speed at which depth information can be extracted from a scene, structured light depth extraction methods have been developed. In structured light depth extraction, a projector projects known patterns of structured light, such as lines, circles, bitmaps, or boxes, onto an object. A camera is positioned off-axis from the projector to sample light reflected from the object. A computer connected to the camera and the projector calculates depth information for the object of interest based on the projected light patterns, the reflected light patterns sampled by the camera, the position and orientation of the camera, and the position and orientation of the projector.

In early structured light depth extraction systems, slide projectors were utilized to project structured light patterns onto an object of interest. In order to project a plurality of patterns onto the object, a human operator manually placed slides containing different patterns in the slide projector. The slide projector projected the structured light patterns onto the object. A camera positioned off-axis from the slide projector sampled the reflected light for each structured light pattern. The sampled images were input into a computer that calculated depth information for the object. While these early systems were capable of accurate depth calculations, they were too slow for real-time updating of a displayed image.

More recently, structured light depth extraction has been performed using video projectors capable of changing structured light patterns about twice per second, resulting in updating of a displayed three-dimensional image about once every eight seconds. These structured light depth extraction systems may be capable of determining depth information more rapidly than conventional structured light depth extraction systems or laser scanned depth extraction systems. However, these systems are still too slow for real-time applications.

One application in which it may be desirable to use structured light depth extraction is endoscopy, where it is desirable to display a real-time image of the interior of a patient's body. In endoscopic surgery, an endoscope including or connected to a camera is inserted in a first incision in a patient's body, while a surgeon operates through another incision in the patient's body. The surgeon views the image seen by the camera on a video screen in order to guide surgical instruments in performing the operation. The image displayed on the video screen must be updated in real time, such that movements of the patient and the surgeon are reflected in the image with minimal latency. Currently, video cameras used in endoscopic surgery produce an image that is updated 30 times per second. As stated above, conventional structured light depth extraction systems are capable of updating a displayed image only about once every eight seconds. Thus, conventional structured light depth extraction systems are too slow for endoscopic surgical applications.

Another problem associated with applying structured light depth extraction systems to endoscopic surgery is that objects inside a patient's body are often wet and thus produce bright specular reflections. These reflections may saturate the phototransistors of a camera sampling the reflections. Saturating the phototransistors of the camera may lead to inaccurate reproduction of the scene. As a result, conventional structured light depth extraction is unsuitable for endoscopic surgical applications.

Conventional endoscopes include or are connected to one or more cameras that allow the surgeon to view the interior of the patient's body without utilizing structured light depth extraction. A single-camera endoscope is incapable of communicating depth information to the surgeon, unless the camera is continuously moving. Such continuous motion may make some tasks more difficult, may require a robot arm to guide the camera, and may result in trauma to the patient. In an alternative method, in order to determine depth information using a single-camera endoscope, the surgeon may either probe objects with an instrument or move the endoscope to different locations in the patient's body. Such probing and movement inside the patient's body is undesirable as it may increase trauma to the patient. Stereo endoscopes are capable of showing depth information; however, such devices may not accurately provide depth information with regard to complex rounded objects, such as structures inside a patient's body. Stereo endoscopes are generally used to directly display stereo images to a surgeon. In addition, conventional stereo endoscopes are large in cross-sectional area, thus requiring larger incisions in the patient.

Another problem associated with conventional endoscopic surgical instruments is that the camera may not view an object from the same direction that the surgeon is facing. As a result, movements of a surgical instrument viewed on the display screen may not match movements of the surgeon's hands operating the instrument. Thus, the surgeon is required to have excellent hand-eye coordination and experience in operating a conventional endoscope.

In light of the problems associated with conventional endoscopes and the inability of conventional structured light depth extraction systems to provide depth information in real time, there exists a need for real-time structured light depth extraction systems and endoscopes including real-time structured light depth extraction systems.

DISCLOSURE OF THE INVENTION

An object of the invention is to provide a real-time structured light depth extraction system and an endoscope having a real-time structured light depth extraction system.

Another object of the present invention is to provide an endoscope with a shared optical path for multiple optical signals so that the cross-sectional area of the endoscope can be made smaller.

Another object of the present invention is to provide an augmented reality visualization system for endoscopic surgery having a real-time structured light depth extraction system.

According to a first aspect, the present invention includes a real-time structured light dept extraction system. The system includes a projector, a camera, and an image processor/controller. The projector includes a light source and a display screen. The display screen displays first and second reflective patterns. The second pattern is the inverse of the first pattern. The light from the light source reflects from the reflective patterns to create structured light patterns that are projected onto an object of interest. The camera samples light reflected from the object during projection of both the first and second structured light patterns and outputs digital signals to the image processor/controller. The image processor/controller processes the digital signals and extracts depth information of the object in real time.

As used herein, the phrase "real-time" refers to perceived real time from the point of view of a human observer. For example, in a real-time structured light depth extraction system, depth information relating to an object being viewed is determined at a sufficiently high rate for updates to a displayed image to appear continuous to a human observer. In order to appear continuous to a human observer, the updates may occur at a rate of at least about 10 updates per second. More preferably, the updates may occur at a rate of at least about 15 updates per second. Even more preferably, the updates may occur at a rate of at least about 30 updates per second. An update rate of 30 updates per second corresponds to a standard video frame rate.

As used herein, the phrase "depth information" refers to information relating to the distance between an object being viewed by a camera and the camera image plane. The depth information may be the actual distance value or information intermediate to calculating the actual distance value.

According to another aspect, the present invention includes an endoscope having a shared optical path for multiple signals. For example, in endoscopes that use real-time structured light depth extraction, optical signals from the projector and optical signals reflected from the object of interest may share an optical path within the endoscope. In stereo endoscopes, optical signals reflected from an object and entering the endoscope through separate objective lenses may share a common optical path within the endoscope. In order for different optical signals to share a common path inside the endoscope, the optical signals are polarized in directions that are angularly offset from each other. The amount of offset is preferably 90 degrees, in order to enhance contrast between the optical signals.

According to another aspect, the present invention includes an augmented reality visualization system for endoscopic surgery that utilizes real-time structured light depth extraction to determine depth information relating to the inside of a patient's body. A graphics generator generates synthetic images to be merged with real images and displayed to a viewer, such as a surgeon. An image merger merges the real and synthetic images such that the objects in the final images have proper occlusion relationships. A display, such as a head-mounted display, displays the merged images to the viewer.

While some of the objects of the invention have been stated hereinabove, other objects will become evident as the description proceeds, when taken in connection with the accompanying drawings as best described hereinbelow.

BRIEF DESCRIPTION OF THE DRAWINGS

The patent or application file contains at least one drawing executed in color. Copies of this patent with color drawing(s) will be provided by the Patent and Trademark Office upon request and payment of necessary fee.

Embodiments of the present invention will now be described with reference to the accompanying drawings, of which.

BEST MODE FOR CARRYING OUT THE INVENTION

Real-Time Structured Light Depth Extraction System

Figure 1:
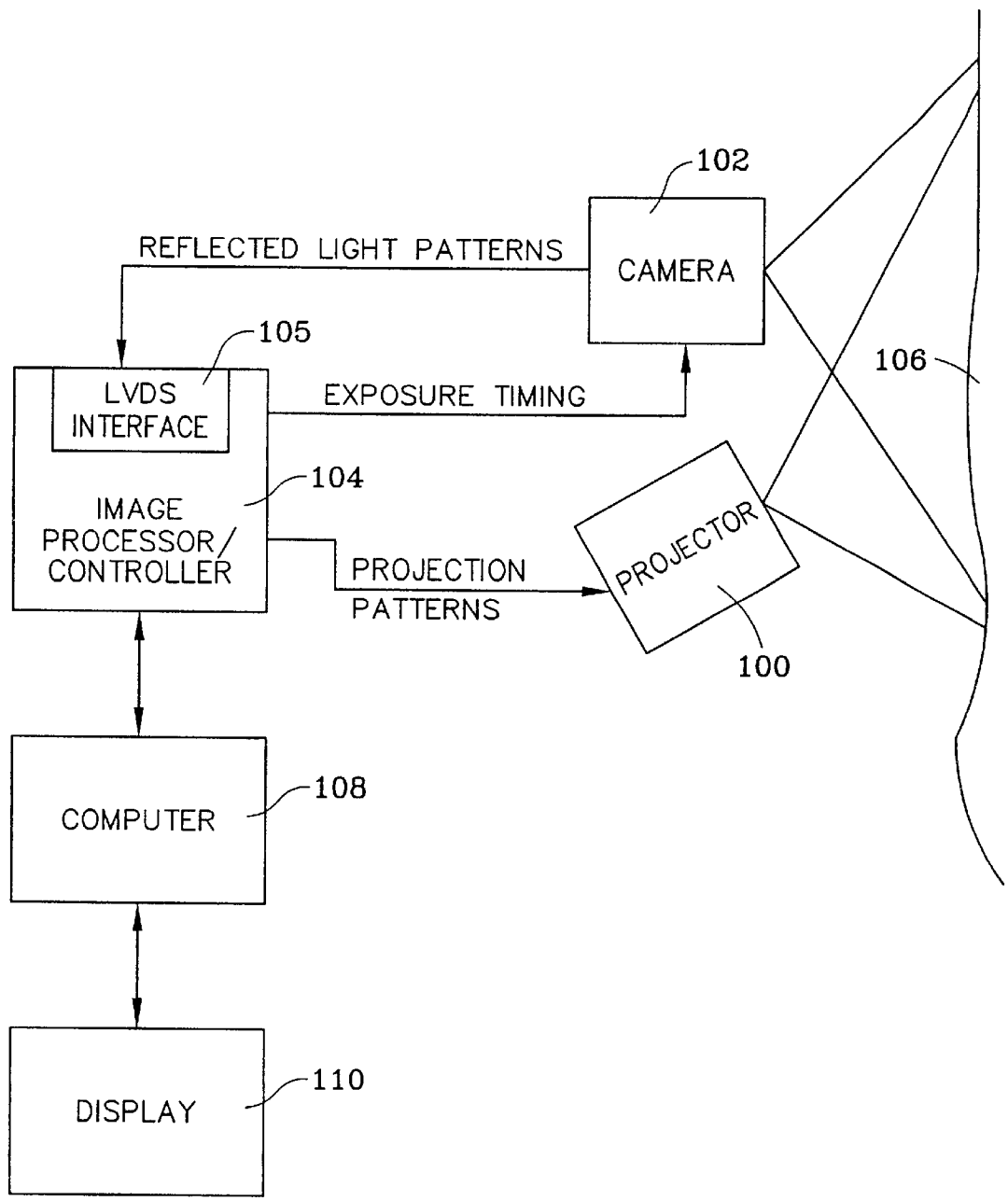
FIG. 1 is a block diagram of a real-time structured light depth extraction system according to an embodiment of the present invention.

FIG. 1 illustrates a real-time structured light depth extraction system according to a preferred embodiment of the present invention. In the illustrated embodiment, a projector 100, a camera 102, and an image processor/controller 104 cooperate to extract depth information of an object 106. A computer 108 may assist in extracting the depth information and outputting three-dimensional images to a display 110. Each of the components illustrated in FIG. 1 will now be discussed in more detail.

The projector 100 may be any projector capable of projecting patterns of structured light onto the object 106 at a high rate of speed. In order to achieve a high pattern projection rate, the projector may include a reflective display device, such as a ferro-reflective liquid crystal display (LCD) device, for displaying reflective patterns and rapidly refreshing the displayed patterns. Prior to the present invention, ferro-reflective LCDs were used primarily to display video information to a user. For example, one conventional use of ferro-reflective LCDs is displaying video to a user through a head-mounted display. Ferro-reflective LCDs are used in the present embodiment to generate patterns that reflect light onto an object of interest.

Exemplary ferro-reflective LCDs suitable for use with the present invention are available from Displaytech, Inc. One exemplary Displaytech display that may be used has a display screen with a refresh rate of 180 Hz and a resolution of 640×480 pixels. This reflective display device is conventionally used to display color video information to a viewer at a frame rate of 30 frames per second. In order to display color video images to the viewer, red, green, and blue light-emitting diodes (LEDs) project red, green, and blue light onto the patterns displayed on the reflective display device during each thirtieth of one second. In order to prevent crystal migration, the reflective display device displays a negative or inverse version of each pattern following the display of the positive pattern. For example, during a first display period, some pixels on the display are ON and others are OFF. During the next display period, all pixels that were ON during the first display period are OFF, and all pixels that were OFF are ON. The LEDs used to generate color video are conventionally turned OFF during display of the inverse pattern. According to the present embodiment, the red, green, and blue LEDs are replaced by a constant light source, which preferably remains ON during display of both the positive and negative patterns, resulting in the projection of 180 patterns per second. The camera 102 preferably samples the reflected light during both the positive and negative display periods. The image processor/controller 104 utilizes reflected light during both the positive and negative patterns to determine depth information.

Keeping the light source ON and sampling the reflected images during display of both the positive and negative patterns greatly increases the speed at which structured light patterns are projected and the corresponding speed at which depth information is determined. For example, since the Displaytech display described above has a refresh rate of 180 patterns per second, the rate at which structured light patterns are projected and sampled is 180 patterns per second. However, the present invention is not limited to projecting 180 patterns per second. For example, the present invention is capable of projecting patterns at higher rates as display refresh rates increase.

As discussed above, in order to generate structured light patterns, light from a constant light source is projected onto the patterns displayed by the display device and reflected onto the object of interest. The light source may be any type of light source, for example, an incandescent bulb. In order to avoid thermal damage to the object being viewed or the display screen, the light source is preferably a cold light source. A cold light source includes an infrared filter or reflector at the output of the light-emitting element that filters infrared energy from the output light beam. The infrared energy may be dissipated by any suitable means, such as a heat sink.

The wavelength of the light output from the light source is preferably selected to enhance the structured light depth extraction. In a preferred embodiment of the invention, the wavelength of the light output from the cold light source is in the visible range. For example, the wavelength of the light output from the light source may range from about 450 nm to about 720 nm. When extracting depth information, the light output from the light source is preferably white light. However, as will be discussed in more detail below, the light output from the light source may be filtered to produce other colors, such as red, green, and blue, to determine color information of the object being viewed.

The camera 102 may comprise any camera capable of sampling reflected light from the object 106 in synchronism with the projection of patterns by the projector 100 and outputting digital signals based on the sampled images at the same or close to the same rate. For example, if the projector is capable of projecting structured light patterns at a rate of 180 patterns per second, the camera 102 is preferably capable of sampling at least 180 patterns per second and outputting digital signals indicative of the patterns. Another desirable characteristic of a high speed camera according to the present embodiment is that the camera have sufficient resolution for structured light depth extraction. For example, the resolution of the camera is preferably at least as high as the resolution of the projected structured light patterns. More preferably, the resolution of the camera is higher than the resolution of the projector to allow oversampling and/or better discerning between adjacent pixels.

An exemplary high speed camera suitable for real-time structured light depth extraction according to the present embodiment is the DA-512 available from Dalsa Corporation. This camera is conventionally used for applications requiring high speed image capture, such as robotics-controlled manufacturing. The DA-512 is a 512×532 pixel monochromatic camera capable of sampling and outputting up to 264 frames per second in low voltage differential signal (LVDS) format. Outputting signals in digital format, such as LVDS format, is preferable over analog format because it reduces the amount of processing required later to determine depth and facilitates synchronization with the projector. In an alternative embodiment, the camera may output signals in analog format and an analog-to-digital converter may be used to convert the signals into digital format. In addition, the present invention is not limited to using a monochromatic camera. For example, in an alternative embodiment, the camera 102 may comprise a color camera.

The image processor/controller 104 may comprise any device capable of receiving and efficiently processing the digital signals from the camera 102. For example, the image processor/controller 104 may comprise a printed circuit board with an on-board processor and on-board memory for image processing. The image processor/controller 104 may interface with the computer 108 for additional image processing and storage capabilities. For example, the computer 108 may comprise a personal computer and the image processor/controller 104 may comprise an adapter card compatible with a standard interface, such as a PCI interface, of the computer 108. In order to increase image processing speed, the image processor/controller 104 may include a hardware-encoded instruction set tailored for image processing. Storing the sampled data in an on-board memory device and processing the data using a hardware-encoded image processing instruction set increases the speed at which depth information is determined by reducing the number of accesses to main memory of the computer 108.

An exemplary image processor/controller that may be suitable for real-time structured light depth extraction according to the present embodiment is the Genesis graphics card available from Matrox Corporation. In an alternative embodiment, the image processor/controller may comprise an Onyx Infinite Reality system available from Silicon Graphics, Inc. A digital interface, such as an LVDS interface 105, may be used to receive the signals from the camera. However, the present invention is not limited to using an LVDS interface to receive the digital data from the camera. Any interface that corresponds to the data output from the camera is within the scope of the present invention.

The image processor/controller 104 preferably performs at least some of the calculations required to extract depth information based on the digital data received from the camera. For example, as will be discussed in more detail below, the image processor/controller 104 may perform pixel classification, wherein pixels in the sampled images are identified in the projected image. The image processor/controller 104 may also determine the divergence between pixels in the projected and sampled images. Divergence is the distance between the actual and expected pixel location in the sampled image. This distance may be used to calculate depth information. The actual calculation of depth values may be performed by the image processor/controller 104 and output to the computer 108. Alternatively, the image processor/controller 104 may output a divergence value for each pixel and the divergence value may be output to the computer 108 for depth calculation. Any manner of sharing the calculation of depth information between the image processor/controller 104 and the computer 108 is within the scope of the invention. The depth information determined by the image processor/controller 104 and/or the computer 108 may be used to update an image displayed on the display device 110.

The display device 110 may be any type of display device suitable for displaying computer-generated images, e.g., a cathode ray tube or an LCD. The depth information is preferably determined at a sufficient rate to enable the displayed image to be updated in real-time. For example, if the object being viewed moves or the angle from which the object is being viewed changes, the image on the screen is preferably updated at a sufficient rate for the changes to appear continuous to a human observer. In order to appear continuous, the displayed image is preferably updated at a rate of at least about 10 updates per second, more preferably, at a rate of at least about 15 updates per second, and, even more preferably at a rate of at least about 30 updates per second. Because the projector is capable of projecting high resolution structured light patterns at a rate corresponding to the refresh rate of the display screen used to produce the patterns, the camera samples both positive and negative structured light patterns, and the image processor/controller 104 is optimized for image processing, the present embodiment is capable of real-time updates to the displayed image.

For example, the Displaytech projector, when operated as described above, is capable of projecting 180 patterns per second. The Dalsa DA-512 camera is capable of sampling the reflected patterns at the projection rate and outputting signals indicative of the samples in LVDS format. An LVDS board coupled to the Matrox Genesis processor receives the samples. The Matrox Genesis processor then processes the samples at high speed to extract depth information. Several reflected images may be required in order to determine depth or Z buffer values for the pixels in an image. However, even if 10 reflected patterns, e.g., 5 positive patterns and 5 negative patterns, are required to extract depth information from an object, real-time rates of 18 updates per second can be achieved.

In addition to receiving and processing the digital signals output from the camera 102, the image processor/controller 104 may also control the camera 102 and the projector 100. For example, the image processor/controller 104 may store projection patterns in local memory to be displayed by the projector. Alternatively, the image processor/controller 104 may access main memory of the computer 108 to extract image data. The image processor/controller 104 may also control the timing of the projection of structured light patterns by the projector and the timing of the opening and closing of the camera shutter. For example, in the illustrated embodiment, the image processor/controller 104 outputs an exposure timing signal to control the opening and closing of the camera shutter. The image processor/controller 104 also outputs projection patterns to the projector 100. In an alternative arrangement, these patterns may be output from a monitor port of the computer 108.

Pixel Classification

In order to determine depth information using structured light, pixels from the projected structured light pattern are identified or classified in the reflected light pattern. Depth or range information can then be determined from the relationship between the positions of the pixels in the projected and reflected patterns, the position and orientation of the camera, and the position and orientation of the projector. The depth information may then be used to determine whether one pixel is in front of another pixel in the displayed image. For example, in one exemplary image processing method, pixels in a two-dimensional image have row and column coordinates and a color value. Each pixel also includes a depth or Z buffer value representing the distance between the pixel and the camera image plane. If pixels lie along the same line from a given viewing angle, the pixel with the higher depth value is determined to be behind another pixel with the lower depth value. Thus, the pixel with the lower depth value is displayed and the pixel with the higher depth value is not displayed because it is occluded by the other pixel.

Conditions that may increase the difficulty of identifying pixels in the reflected image include poor contrast, the presence of shadowed objects, and highly specular surfaces. Pixel classification methods and systems according to the present invention preferably reduce the effects of these conditions.

Although any structured light pattern or patterns may be used to extract depth information, the pixel classification method and systems according to the present invention will be explained in the context of projecting patterns of vertical strips onto an object. Other patterns that may be projected include geometric patterns, such as squares, circles, and/or triangles, and bitmaps. In this example, the pixels in the reflected pattern are classified according to the strip in the projected pattern from which the pixel originated. In addition, because the ferro-reflective display device described above generates both positive and negative structured light patterns, the pixel classification algorithm according to the present embodiment preferably uses reflected light from both the positively and negatively lit object to classify pixels.

The following example illustrates a pixel classification algorithm that may be used to classify pixels according to an embodiment of the present invention. In the example, a first vertical strip, strip A, and a second vertical strip, strip B, comprise a structured light pattern that is projected onto an object. In the positive pattern, all of the pixels in strip A may be lit and all of the pixels in strip B may be unlit. In the negative pattern, all of the pixels in strip A may be unlit and all of the pixels in strip B may be lit. According to an exemplary pixel classification algorithm, a pixel in the reflected image may be classified as belonging to strip A if it is lit during the positive image projection and unlit in the negative image projection. Similarly, a pixel may be classified as belonging to strip B if it is unlit in the positive projection and lit in the negative projection. Any pixel that does not fall in one of the two previously described categories may be classified as unusable for depth calculations. Conventional pixel classification algorithms make a binary decision for each pixel. As a result, outlying pixels may adversely affect the accuracy of depth information. The present invention reduces the problem of outlying pixels by classifying those pixels as unusable.

The following steps illustrate an exemplary pixel classification method according to the present invention:

1. Each pixel $P_{i,j}$ from the positive image and each pixel $N_{i,j}$ from the negative image are subtracted from each other and a biasing value B is added to the resulting difference. The result is stored as a summed image $S_{i,j}$. This step may be illustrated by the following equation:

$$S_{i,j}=P_{i,j}-N_{i,j}+B.$$

The biasing value B is preferably selected so it is not possible for any value of $S_{i,j}$ to be negative.

2. If a lit pixel in the original images has an average intensity measured by the camera of L and an unlit pixel has an intensity U, then a pixel meeting the criteria for belonging to strip A should have a value S of approximately:

$$S_A=L-U+B.$$

A pixel belonging to strip B should have a value S of approximately:

$$S_B=U-L+B.$$

The mean difference of value in S between a pixel of strip A and of strip B should thus be:

$$2L-2U.$$

A pixel that does not meet the above-described criteria should not be classified as belonging to either strip A or strip B. Such a pixel may have an intensity that varies in a way that has little correspondence to the lighting condition. For example, the intensity may be represented by a random variable with a mean value of M. Conditions that may cause the presence of such pixels in captured images include pixels lying in shadows, pixels being outside the area directly lit by the projector, or pixels lying on part of a surface with a high degree of specular reflection. In the first two cases, the pixel is lit by ambient light due to light scattered from other surfaces. The total light in the scene is equivalent in both the positive and negative images. Thus, it is reasonable that the value of the pixels at these locations would be equivalent in both images. In the case of specular spots, the same location in both positive and negative images has been observed to saturate or nearly saturate the camera, so that a near maximal value is observed on both images. As a result, the value of S for these points is expected to have a mean value of:

$$S_U=M-N+B=B.$$

3. Given these results, simple thresholding operations may be used to classify each pixel in the original two images.

Figure 2:
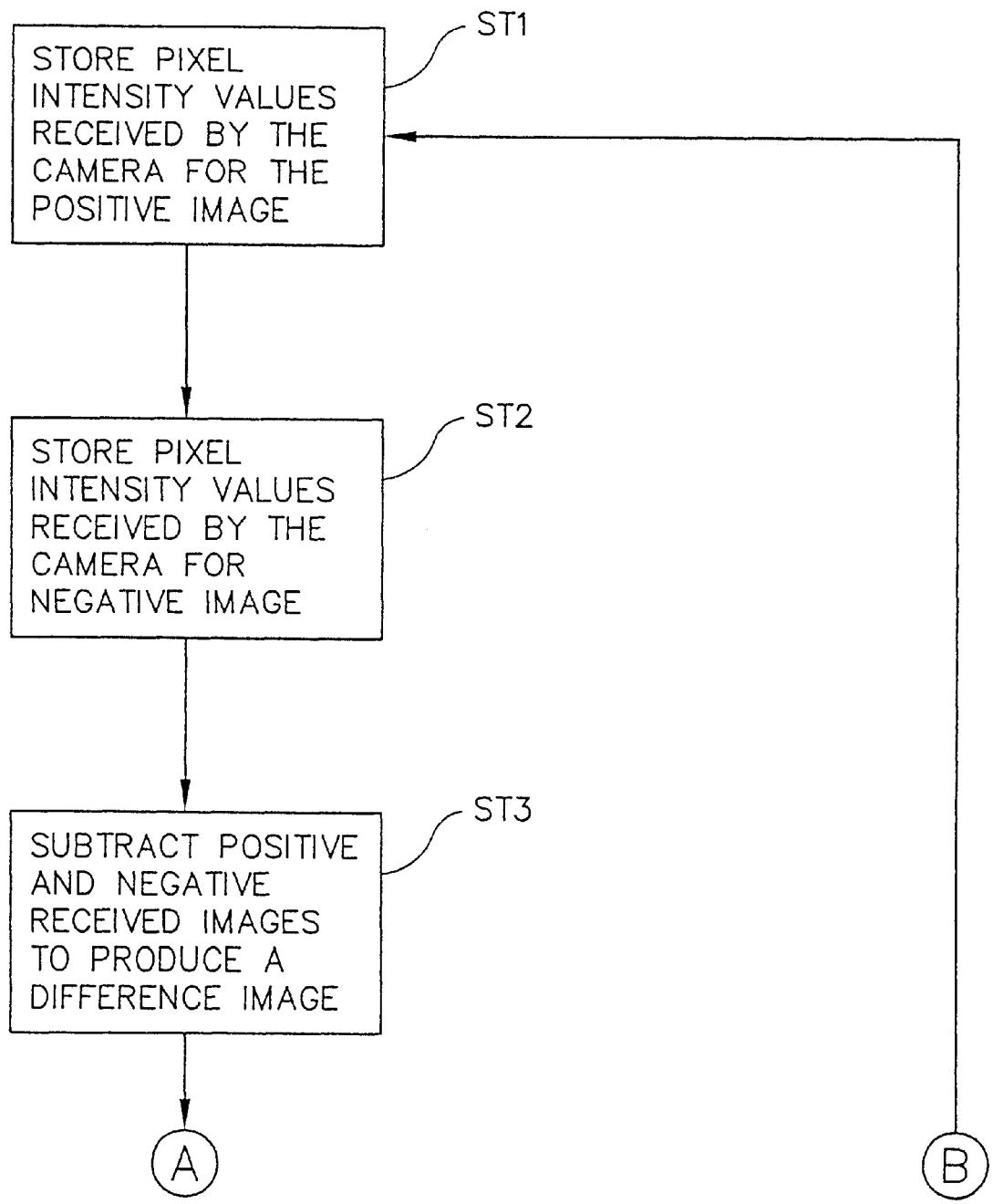
FIGS. 2 and 2(a) illustrate a flow chart of a pixel classification routine according to an embodiment of the present invention.
Figure 2A:
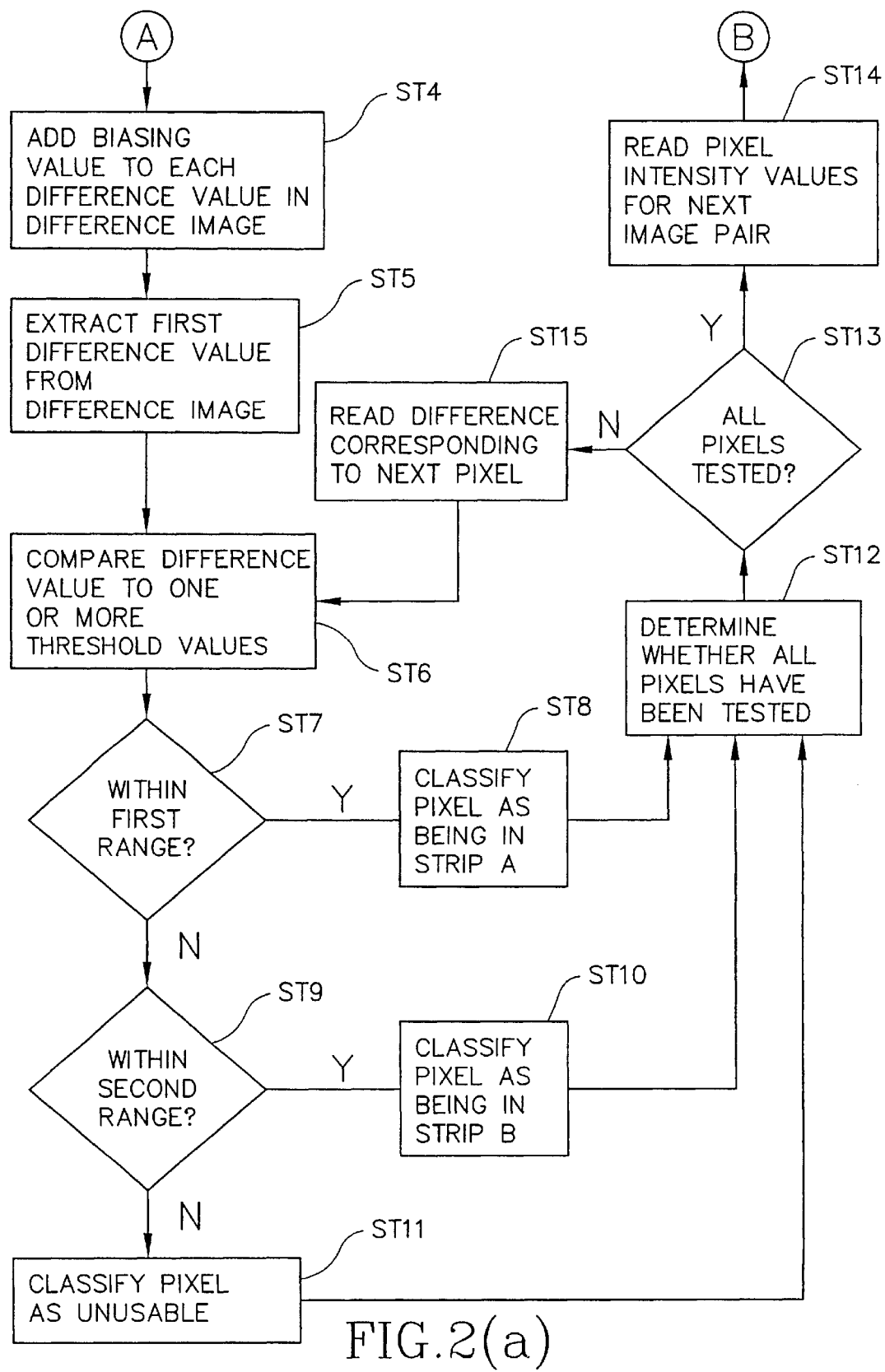

The above-described algorithm may be implemented in hardware, software, or a combination of hardware and software. The algorithm may be executed very rapidly in image processing hardware because it uses simple and commonly implemented image manipulations. FIGS. 2 and 2(a) illustrate is a flow chart illustrating steps of an exemplary pixel classification routine for implementing the pixel classification algorithm described above according to an embodiment of the present invention. In step ST1, the pixel classification routine stores the pixel intensity values received by the camera for the positive image. In step ST2, the pixel classification routine stores pixel values received by the camera for the negative image. Alternatively, the biasing value may be added to the pixel values in the positive and negative images before subtracting the values. In step ST3, the pixel classification routine subtracts the pixel values in the negative image from the pixel values in the positive image to produce a difference image. In step ST4, a biasing value is added to each difference value in the difference image. Alternatively, the biasing value may be added to the pixel values in the positive image before subtracting the values, depending on the data type. In step ST5, the pixel classification routine extracts a first difference value from the difference image. In step ST6, the pixel classification routine compares the extracted difference value to one or more threshold values. If the difference is within a predetermined range centered at the value, L−U+B, the pixel corresponding to the difference may be classified as being in strip A. (steps ST7 and ST8) If the difference is within a predetermined range centered at the value U−L+B, the corresponding pixel may be classified as being in strip B. (steps ST9 and ST10) If the difference does not fall in either of the ranges, the pixel corresponding to the difference may be classified as unusable for determining depth information. (step ST11) In some hardware implementations, steps ST7, ST9, and ST11 may be combined. Once the pixel has been classified, the pixel classification routine determines whether all pixels in the difference image have been tested. (steps ST12 and ST13) If all pixels have been tested, the pixel classification routine may read the pixel intensity values for the next image pair (step ST14) and return to step ST1 to classify pixels for the next image pair. If the differences for all pixels have not been tested, the pixel classification routine reads the difference corresponding to the next pixel (step ST15) and repeats steps ST6–ST13.

The present invention is not limited to the pixel classification routine illustrated in FIGS. 2 and 2(a). For example, the pixel classification routine may identify all unusable pixels in a first pass through the difference image. In the second pass, the pixel classification routine may classify the remaining pixels as belonging to strip A or strip B. Identifying unusable pixels as a preliminary step may reduce the number of comparisons required if the scene being viewed includes shadows or specular reflections.

The pixel classification algorithm described above classifies pixels according to the difference in intensity values between positive and negative images. Unusable pixels are preferably identified and not used in depth calculations. Pixels classified as belonging to one of the patterns in the projected image are used to determine the depth of the object being viewed. For example, for each pixel, given its location in the projected image, its location in the reflected image, the position and orientation of the projector, and the position and orientation of the camera, the depth of a point on the surface of the object can be calculated using known geometric techniques, such as triangulation. The depth values may then be used to determine proper occlusion relationships among displayed pixels when an image is reproduced from a new perspective.

The pixel classification algorithm may also be used to estimate motion between the capture of positive and negative images. The total number of usable and unusable pixels may vary depending upon the degree of noise in the system. However, dramatic increases in the number of unusable pixels may indicate that either the camera and the projector are being moved or the scene itself is being manipulated. Thus, in order to detect motion, the number of unusable pixels during a first projection period may be compared to the number of pixels during a second projection period. If the difference between the number of unusable pixels in the first and second projection periods exceeds a predetermined threshold, the image processor/controller may determine that the scene has moved.

Specularity Reduction Methods

As discussed above, reflections from glossy or wet objects may saturate the light-receiving cells in the camera, thus leading to inaccurate depth calculations. Although a variety of methods may be used to alleviate this problem, one method that may be used according to the present invention is operating the camera at multiple variable-length integration times. The integration time is the time that the camera shutter remains open to sample the reflected image. The principle behind using variable-length integration times is that bright reflections are preferably sampled using short integration times, and dark reflections are preferably sampled using long integration times. The samples taken during the long and short integration times are then added to produce the final image.

Figure 3A:
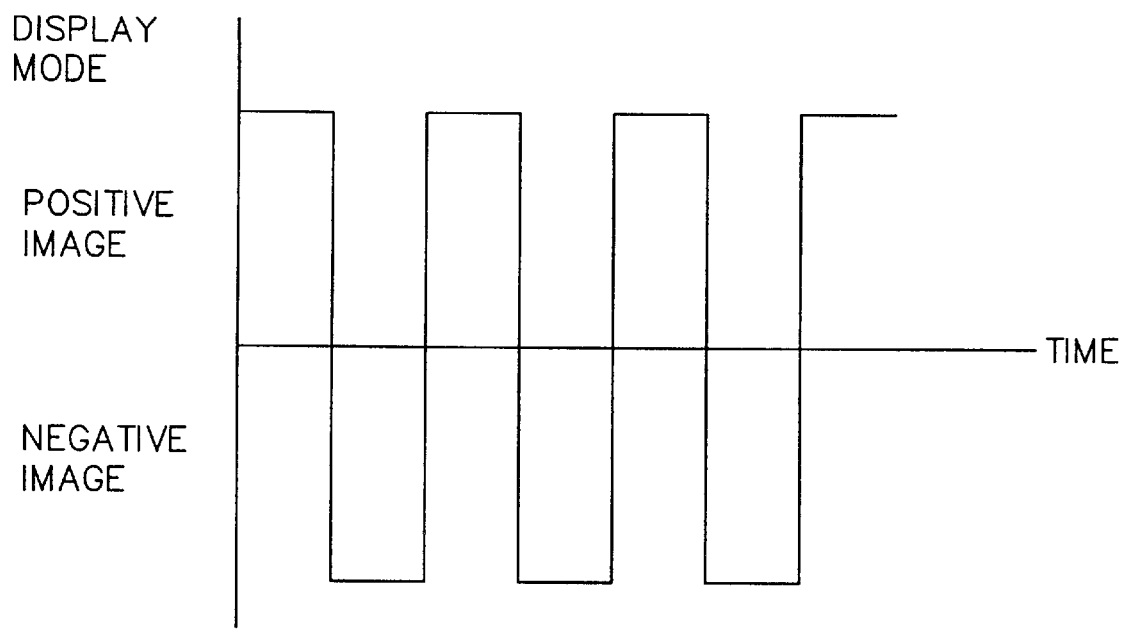
FIGS. 3(a) and 3(b) are timing diagrams illustrating the relationship between the display times for positive and negative images and camera integration times according to an embodiment of the present invention.
Figure 3B:
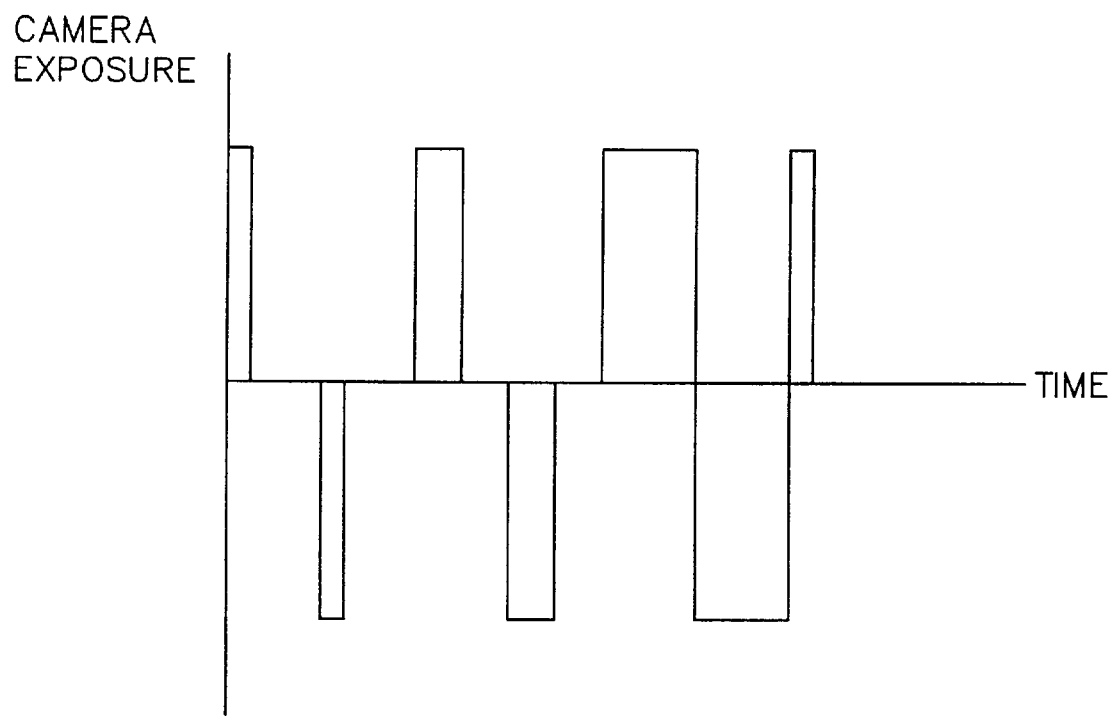

FIGS. 3(a) and 3(b) are timing diagrams respectively illustrating pattern display periods and camera exposure times. For example, the horizontal axis in FIG. 3(a) may represent time and the vertical axis may represent the display mode. When the display mode is positive, a first pattern may be displayed on the display screen of the projector. When the display mode is negative, a second pattern that is the inverse of the first pattern may be displayed on the display screen of the projector. In the illustrated embodiment, the first and second patterns are displayed for equal time periods. However, the present invention is not limited to equal positive and negative display periods.

In FIG. 3(b), the horizontal axis represents time and the vertical axis represents camera exposure. The positive camera exposure pulses represent the opening of the camera shutter during positive pattern display periods. The negative camera exposure pulses represent the opening of the camera shutter during negative pattern display periods. The length of each pulse is the camera exposure or integration time. In the illustrated embodiment, the camera shutter is open during both the positive and negative pattern display periods to capture both positive and negative reflected patterns. However, the integration time may be varied in accordance with the intensity of the reflected signal. If one or more of the light receiving cells of the camera are saturated, the integration time may be decreased until none of the cells are saturated. If the light received by the light receiving cells is below a lower threshold, the integration time may be increased until the light received for each pixel exceeds the threshold. The sampled images from the various integration times may be combined to produce a final image with reduced white areas caused by specular reflections and reduced dark areas caused by shadows.

Figure 4:
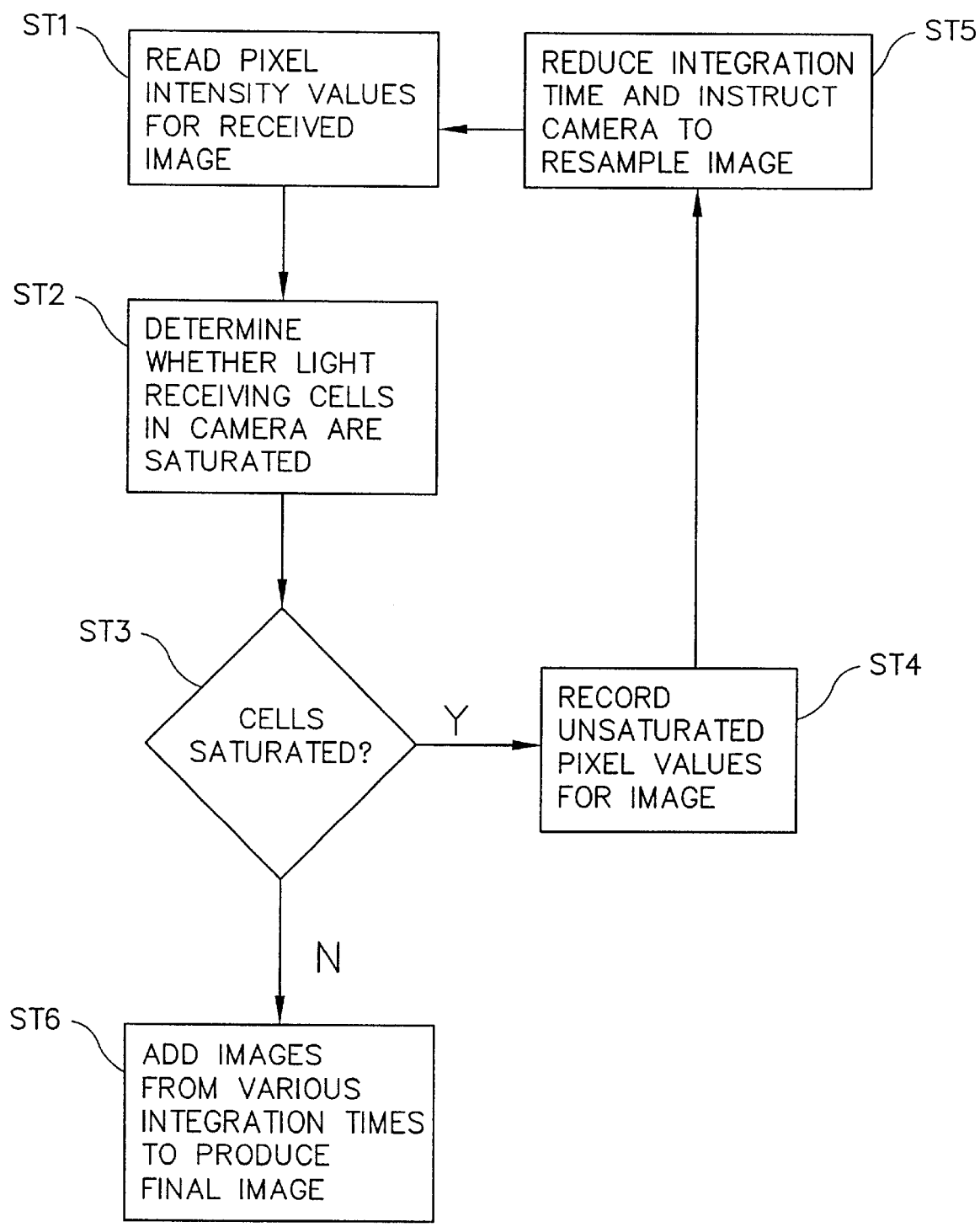
FIG. 4 is a flow chart of a specularity reduction routine according to an embodiment of the present invention.

The specularity reduction method may be implemented in hardware, software, or a combination of hardware and software. FIG. 4 illustrates exemplary steps that may be performed by a specularity reduction routine according to the present invention. In step ST1, the specularity reduction routine reads the pixel intensity values sampled by the camera. In steps ST2 and ST3, the specularity reduction routine determines whether light-receiving cells in the camera are saturated. Determining whether light-receiving cells are saturated may include determining whether a cell records a maximum intensity value. For example, for a camera with 8 bits for representing pixel intensity, a receiving cell recording an intensity value of 255 may be identified as saturated. In step ST4, if one or more of the light-receiving cells are saturated, pixel intensity values for the non-saturated cells are recorded. In step ST5, the specularity reduction routine reduces the integration time and instructs the camera to re-sample the image using the reduced integration time. The routine then repeats steps ST1–ST5 until none of the light receiving cells are saturated. When this occurs, the routine adds or integrates the images recorded for each iteration to produce a final image. (step ST6) Because the effects of specular reflections on the final image are reduced, the accuracy of subsequent depth calculations is increased.

Another method for reducing the effects of reflections from shiny objects according to the invention includes estimating the actual amount of light reaching the target object at each point. Conventional structured light processing is based on analysis and pattern matching of the camera image with the projected image, wherein image processing operations focus on edge detection or contrast enhancement. According to the present method, the captured camera image and real-time calibrations are used to estimate the actual amount of light reaching the target surface at each point. In order to determine the actual amount of light reaching the surface or the incident intensity, from the camera image, a mapping from camera pixel intensity to incident pixel intensity is determined. According to the present method, this mapping may be determined by projecting several grayscale images of increasing intensity, then capturing the resulting camera images at varying exposure times. This sampling provides a linear intensity response function for every pixel in the camera field. Once the mapping is determined, the mapping can be used to estimate incident intensities from camera intensities when sampling the camera field. As a result, the projected image can be reconstructed from the camera data, and reconstruction of the object is ideally independent of target optical characteristics.

To ensure that the previously described intensity response function is linear, it is preferable to prevent the camera from saturating at any of the sampling configurations. Standard cameras may not have enough color depth to prevent saturation. Multiple camera and/or projector frames can be used to effectively increase the color or brightness depth of the images by varying the projection and integration times of the projectors and cameras, i.e., by using sub-frames to multiple frames, if necessary. Increasing the pixel depth will provide the linearity necessary for the previously described incident pixel estimation method to work correctly.

Extracting Color from High Speed Structured Light Using Monochromatic Camera As discussed above, the camera utilized to sample structured light images may be a monochromatic camera. However, according to another aspect of the invention, color information of a scene may be extracted from received structured light patterns, even though the camera is monochromatic. In order to extract color information using a monochromatic camera, a color wheel, such as a mechanical color wheel, may be positioned at the output of the light source of the projector. The color wheel rotates, causing red, green, and blue patterns to be projected onto the object. Portions of the object that are red will produce a high-intensity reflected light pattern when illuminated by red light. Yellow and green portions of the object will not produce a high intensity reflected light pattern when illuminated by red light. Thus, when the monochromatic camera receives a high-intensity light signal and the projected light is red, this signal will be classified as red. The process is preferably repeated for blue and green to identify blue and green areas in the object being viewed.

In order to produce a full-color, full-camera-resolution output image, the images sampled by the camera during the red, green, and blue projection times may be combined, for example, by the image processor/controller 104 illustrated in FIG. 1. In addition, depth information and color information may be extracted simultaneously during projection of colored structured light patterns. However, depth extraction is more efficient when color patterns are not being projected. Thus, color shutters may not be utilized during every projected frame.

Figure 5:
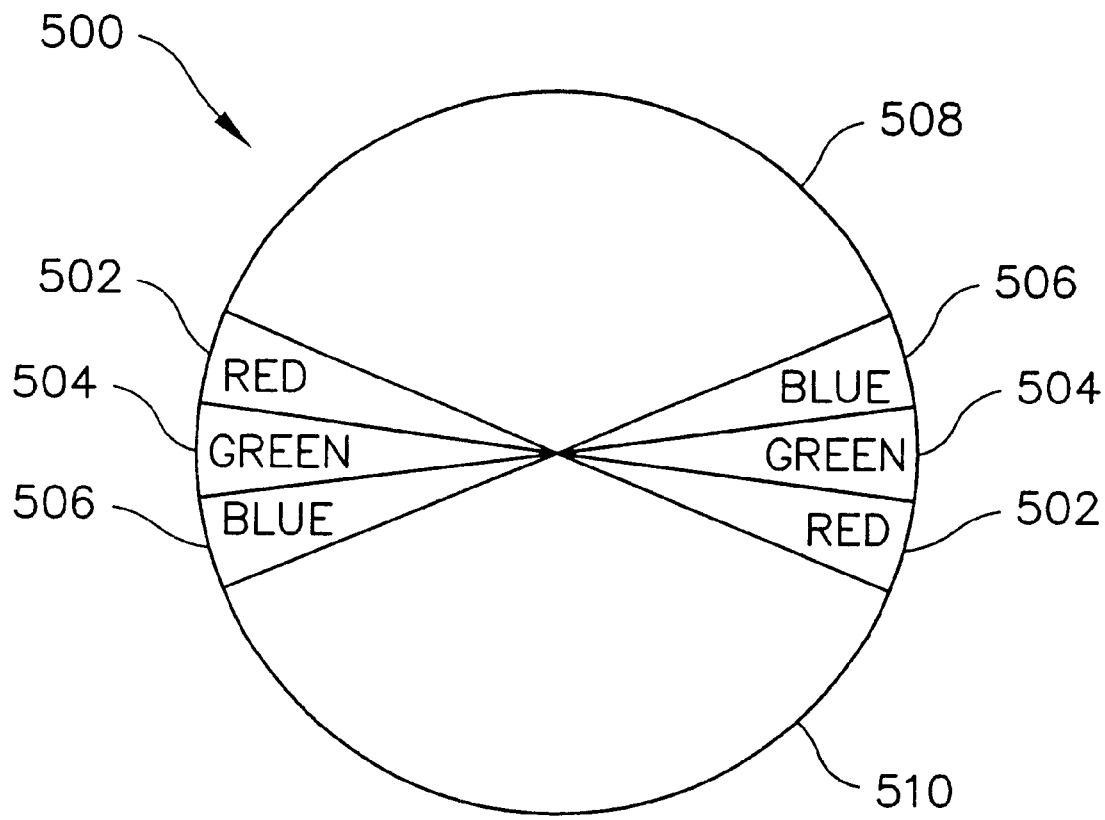
FIG. 5 is a side view of a color wheel that may be used to extract color data from a scene using a monochromatic camera according to an embodiment of the present invention.

FIG. 5 illustrates an exemplary mechanical color wheel 500 that may be used for reduced color resolving time. In the illustrated embodiment, the color wheel includes red, green, and blue areas 502, 504, and 506, used to filter the light output from the light source of the projector. The color wheel 500 also includes transparent areas 508 and 510 that allow light from the projector to pass without altering the color. Because the transparent areas 508 and 510 are larger than the colored areas, the time for color resolution is less than the time for depth extraction without color resolution. As a result, the speed at which depth information is extracted is increased. The color wheel is preferably synchronized with the structured light patterns output from the projector.

The present invention is not limited to the color wheel illustrated in FIG. 5. The proportions of the colored areas with respect to the transparent areas may be changed in accordance with the application. For example, if the structured light depth extraction system is being used in an environment where colors of a scene change frequently and depth does not, it may be desirable to increase the proportion of colored areas with respect to the transparent areas. Alternatively, in applications where depth changes frequently but color does not, the size of the colored areas may be decreased. Any proportion of color and transparent areas is within the scope of the invention.

Thus, according to the present embodiment, color images can be acquired, even when using a monochromatic camera, by using a color wheel and analyzing the received image intensity for each of the projected colors. The resulting images for each color projection period are added during image processing to produce a full color image. Commercial systems that provide color images are dependent upon color camera technology. According to the present embodiment, both color and depth images can be acquired using a single camera and no multi-camera clusters are necessary. The color shuttering using a color wheel need not be performed for all frame grabs. For example, the color shuttering is preferably done periodically to optimize depth extraction times.

Endoscope using Real-Time Structured Light Depth Extraction

The methods and systems described above for real-time structured light depth extraction may be used in any application where high-speed determination of depth information associated with an object is desirable. One particular application in which it may be desirable to utilize real-time structured depth extraction is endoscopic surgery, such as laparoscopic surgery, arthroscopic surgery, or any other type of surgery where a camera is used to view the interior of the patient's body. In endoscopic surgery, the structured light projector, camera, and image processor/controller described with respect to FIG. 1 may be used to determine depth information relating to the interior of a patient's body in real time.

Figure 6:
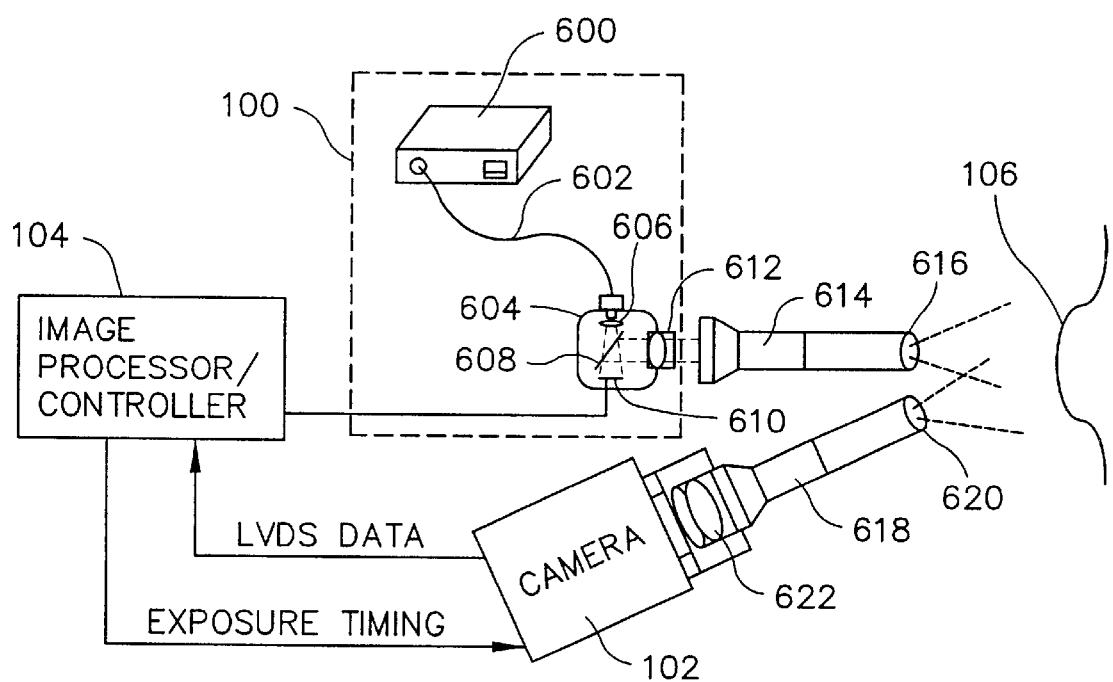
FIG. 6 is a schematic diagram of a real-time structured light depth extraction system for use in laparoscopic surgery according to an embodiment of the present invention.

FIG. 6 is a schematic diagram of a real-time structured light depth extraction system for use in a laparoscopic environment. The illustrated system includes a projector 100, a camera 102, and an image processor/controller 104, as previously described. The projector 100 includes a light source 600, preferably a cold light source, as previously described. The light source 600 is optically coupled through a cable 602 to a projector housing 604. A lens 606 located within the projector housing 604 focuses the light to the input of a polarizing beam splitter 608. The polarizing beam splitter 608 linearly polarizes the light before the light impacts a reflective display 610, such as a ferro-reflective LCD. The display 610 produces reflective patterns under control of the image processor/controller 104. The polarized light from the polarizing beam splitter 608 reflects from the patterns on the display, back to the polarizing beam splitter 608, and through a lens system 612. The lens system 612 directs the structured light patterns into the interior of a laparoscope 614. The laparoscope 614 may include relay optics to direct the structured light patterns through the laparoscopic housing. The structured light patterns exit the laparoscopic housing through an objective lens 616 mounted in the end of the laparoscope and impact the object of interest 106. In a laparoscopic environment, the object of interest 106 may be a surface inside of a patient's body.

A second laparoscope 618 receives the light patterns reflected from the object 106. The second laparoscope 618 may include an end-mounted objective lens 620 and relay optics to receive and transmit the reflected light patterns through the interior of the laparoscope 618. A lens system 622 may focus the reflected light patterns on the imaging system of the camera 102. The camera 102 samples the reflected light patterns at fixed or variable intervals, as discussed above, and outputs a digital signal indicative of the samples. The image processor/controller 104 receives the signals output from the camera 102, and performs some or all of the calculations required for real-time structured light depth extraction, as previously described. Because the system illustrated in FIG. 6 is capable of real-time structured light depth extraction, images including depth information can be displayed to a surgeon and updated in real time.

Endoscope with Shared Optical Path

One problem associated with conventional endoscopes, such as stereo laparoscopes, is that the use of more than one laparoscopic camera has conventionally required multiple separate optical paths for receiving reflected light to be input into the cameras. Separate optical paths may require separate laparoscopes or a single laparoscope of large cross-sectional area. Similarly, in the structured light depth extraction system for laparoscopic use illustrated in FIG. 6, separate laparoscopes for projecting and receiving light are utilized. Because the number and size of the laparoscopes determines the number and size of incisions in a patient's body, a single laparoscope with a reduced cross-sectional area is preferred.

One method for reducing the size of a conventional laparoscope is to utilize a shared optical path for multiple optical signals. For example, in a stereo laparoscope, optical signals reflected from an object through separate objective lenses of the laparoscope may travel through a common optical path within the laparoscope. Similarly, in laparoscopes with real-time structured light depth extraction systems, projected light may share an optical path with reflected light within the laparoscope.

In order for different optical signals to share an optical path within a laparoscope, the optical signals are preferably polarized in directions that are angularly offset from each other. For maximum contrast between two optical signals, the optical signals may be linearly polarized in directions that are offset by 90 degrees from each other.

Figure 7:
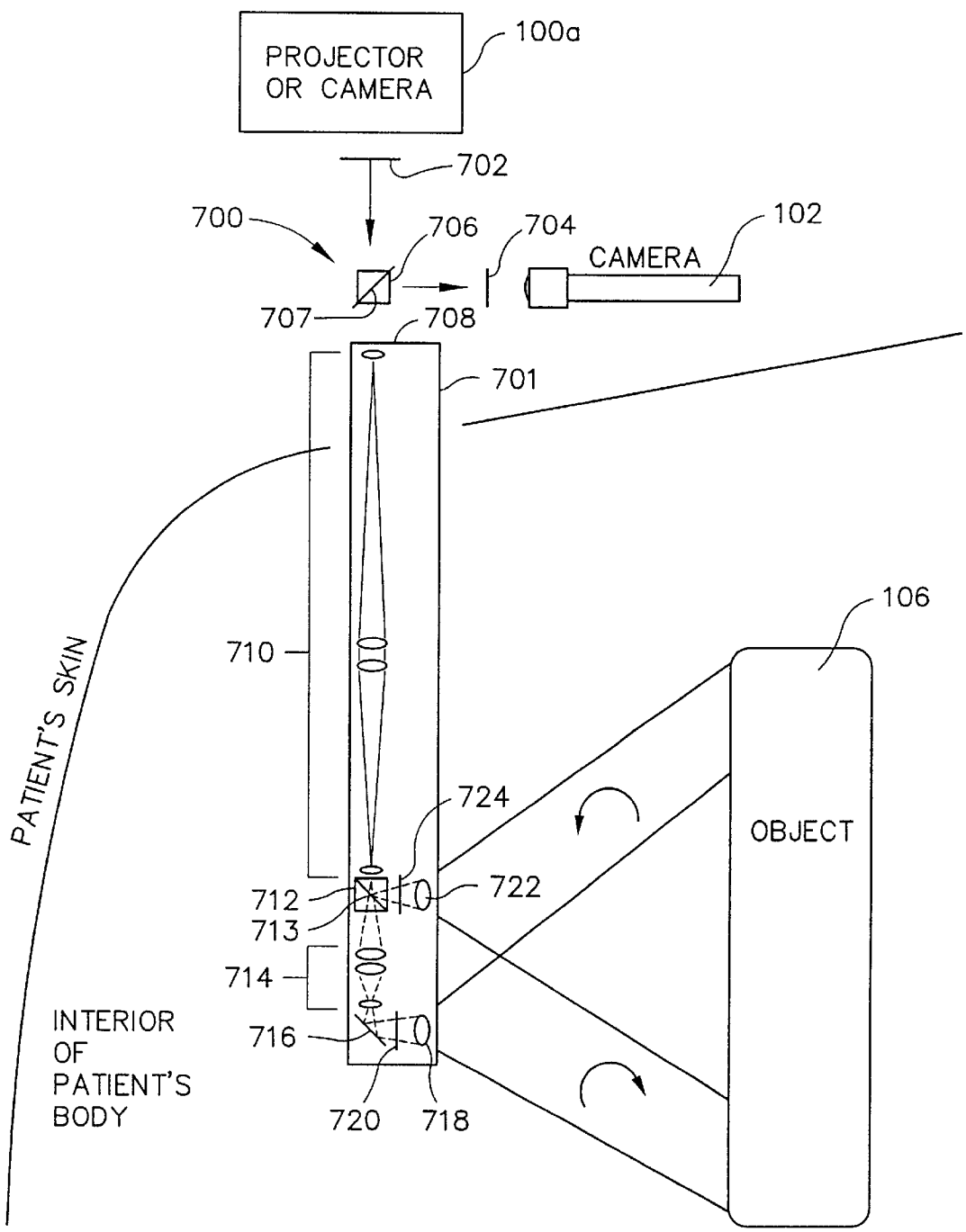
FIG. 7 is an optical schematic diagram of a depth extraction system including a laparoscope having a shared optical path for multiple optical signals according to an embodiment of the present invention.

FIG. 7 is an optical schematic diagram of depth extraction system including a laparoscope 700 having a shared optical path according to an embodiment of the present invention. The laparoscope 700 may be utilized in stereo mode or in real-time structured light depth extraction mode. In stereo mode, the laparoscope 700 may deliver images reflected from an object through two side-mounted objective lenses to two cameras. Accordingly, in stereo mode, block 100a may represent a camera, in addition to the camera 102. In real-time structured light depth extraction mode, the laparoscope 700 may transmit light output from a projector and light reflected from an object through a common optical path. Accordingly, in real-time structured light depth extraction mode, the block 100a may represent a projector. Either or both uses of the laparoscope 700 are within the scope of the invention. In addition, although the present embodiment is described with reference to the laparoscope 700, any type of endoscope is within the scope of the invention. For example, in an alternative embodiment, the laparoscope 700 may comprise an arthroscope.

Real-Time Structured Light Depth Extraction Mode

In real-time structured light depth extraction mode, the system illustrated in FIG. 7 includes a projector 100a, a camera 102, and the laparoscope 700. The laparoscope 700 includes a shared optical path for projected and reflected light bounded by the housing 701. The projector 100a and the camera 102 may comprise any of the high speed projectors or cameras previously described. The system preferably also includes an image processor/controller (not shown in FIG. 7) for processing the images sampled by the camera 102 to extract depth. A first linear polarizer 702 may be positioned at the output of the projector 100a to pass light output from the projector 100a that is linearly polarized in a first direction. A second linear polarizer 704 may be positioned at the input of the camera 102 to pass light polarized in a second direction angularly offset from the first direction. In a preferred embodiment of the invention, the first and second directions are offset from each other by about 90 degrees. The first and second linear polarizers 702 and 704 are included in the illustrated system to increase contrast between projected and reflected light patterns. Additional polarizers and beam splitters within the laparoscope perform the necessary polarization of the projected and reflected light. Accordingly, in an alternative embodiment of the invention, the first and second linear polarizers 702 and 704 may be omitted.

In order to allow projected and reflected light patterns to pass through a common optical pathway inside the laparoscope 700, a first polarizing beam splitter 706 may be positioned between the laparoscope 700, the camera 102, and the projector 100a. The first polarizing beam splitter 706 may comprise a pair of right angle prisms coupled to each other with an interference coating on a hypotenuse surface 707. The first polarizing beam splitter 706 is oriented such that light traveling toward the laparoscope passes through the hypotenuse surface and light exiting the laparoscope is reflected from the hypotenuse surface 707 toward the camera 102. In addition, the polarizing beam splitter 706 polarizes light entering the laparoscope in the first direction and light exiting the laparoscope in the second direction.

The laparoscope 700 may include an optical entry/exit opening 708 for receiving projected structured light patterns from the projector 100a and communicating reflected light patterns to the camera 102. One or more cables (not shown), such as optical fiber cables, may couple the projector 100a and the camera 102 to the entry/exit opening 708. A first relay optics system 710 may be positioned at the entry/exit opening 708 to communicate structured light patterns through the interior of the laparoscope 700. The first relay optics system 710 may comprise an arrangement of lenses that communicates light in both directions through the laparoscope with an input to output image ratio of about one to one.

A second polarizing beam splitter 712 allows light output from the first relay optics system 710 that is polarized in the first direction to pass and reflects light that is polarized in the second direction. The second polarizing beam splitter 710 may be similar or identical in structure to the first polarizing beam splitter 706. In the illustrated embodiment, the light entering the laparoscope from the projector is polarized in the first direction. The second polarizing beam splitter 712 preferably allows this light to pass. Light polarized in the second direction is reflected from a hypotenuse surface 713 of the second polarizing beam splitter 712.

A second relay optics system 714 receives the light from the projector output from the second polarizing beam splitter 712. The second relay optics system 714 comprises an arrangement of lenses that communicates the light further into the laparoscope with an input to output image ratio of preferably about one to one. A polarizer 716 may be positioned at the output of the second relay optics system 714 to linearly polarize the light from the projector in the first direction and direct the light towards a first objective lens 718 to impact on the object 106. The first objective lens 718 may be a single lens or a plurality of lenses.

Because objects within a human body may be wet, specular reflections may result when the objects are illuminated by structured light patterns. In order to reduce these reflections, it may be preferable to circularly polarize the light from the projector 100a before the light is projected onto the object of interest. A circular polarizer, such as a quarter-wavelength retarder 720, may be positioned between the polarizer 716 and the first objective lens 718. The quarter-wavelength retarder 720 changes the polarization of the light from the projector from being linearly polarized in the first direction to being circularly polarized a first circular direction, such as a clockwise direction. In addition to reducing specular reflections, projecting circularly polarized light may also increase the amount of reflected light collected by the laparoscope, especially when the object being illuminated is shiny or irregular in shape.

After the projected light is circularly polarized, the light passes through the first objective lens 718. This lens focuses the light on the object 106. When the project light impacts the object 106, the polarization changes direction. For example, if the incident light is circularly polarized in the clockwise direction, the reflected light is circularly polarized in the counterclockwise direction. A second objective lens 722 receives the reflected light. The second objective lens 722 may be a single lens or a plurality of lenses. A second circular polarizer, such as a quarter-wavelength retarder 724 converts the polarization of the reflected light from circular polarization to linear polarization in the second direction. The hypotenuse surface 713 of the second polarizing beam splitter 712 reflects light from the object that is polarized in the second direction towards the optical entry/exit 708. The first relay optics system 710 communicates light through the laparoscope. Because the reflected light is polarized in the second direction and the projected light is polarized in the first direction, both the projected and reflected light can simultaneously occupy the same axial location in the laparoscope 700. In other words, the laparoscope 700 includes a shared optical pathway for projected and reflected light.

The reflected light exits the laparoscope through the entry/exit opening 708. The first polarizing beam splitter 706 reflects the light from the laparoscope towards the camera 102 and also polarizes the light in the second direction. The second polarizer 704 filters the light reflected from the object to increase contrast. The camera 102 samples the reflected light, produces digital signals indicative of the reflected patterns, and outputs the digital signals to the image processor/controller. The image processor/controller processes the sampled images to obtain depth information, as previously described.

Thus, when operated in structured light depth extraction mode, the depth extraction system illustrated in FIG. 7 uses a shared optical path within the laparoscope for transmitted and reflected light. Using a shared optical path allows a single laparoscope with a reduced cross-sectional area to be utilized for transmitting and receiving structured light patterns. As a result, the size and number of incisions made in the patient is reduced.

The present invention is not limited to the laparoscope 700 illustrated in FIG. 7. For example, additional polarizers may be included to increase contrast between projected and reflected light. The additional polarizers may be included inside the laparoscope 700, inside the projector 100a, inside the camera 102, between the laparoscope 700 and the projector 100a, and/or between the laparoscope 700 and the camera 102. Any arrangement of polarizers that polarizes the projected and reflected light in different directions is within the scope of the invention.

Stereo Mode

As stated above, the depth extraction system illustrated in FIG. 7 may be used in stereo mode to produce stereo images of an object, including depth information, without utilizing real-time structured light depth extraction. The components of the laparoscope 700 are the same as those described above for the real-time structured light depth extraction mode and need not be further described. In stereo mode, since no projector is required, block 100a represents a second camera. An external light source (not shown) may be used to illuminate the interior of the patient's body. The external light source preferably emits circularly polarized light into the patient's body, in order to reduce specular reflections and increase the quality of the stereo image. Light reflected from the object 106 enters the laparoscope 700 through the first and second objective lenses 718 and 722. The first quarter-wavelength retarder 720 converts the light received from the object from being circularly polarized to being linearly polarized in the first direction. The reflected light from the first objective lens 718 contacts the polarizer 716 where it is repolarized in the first direction. The light then proceeds through the second relay optics system 714, through the second polarizing beam splitter 712, through the first relay optics system 710, and out of the laparoscopic housing 701. After exiting the housing 701, the light received through the objective lens 718 passes through the first polarizing beam splitter 706, the first polarizer 702, and into the camera 100a. The image processor/controller (not shown in FIG. 7) processes the images sampled by the camera 100a to produce a first video stream to be displayed to the user.

The light received through the second objective lens 722 passes through the second quarter-wavelength retarder 724. The second quarter-wavelength retarder 724 converts the light from being circularly polarized to linearly polarized in the second direction. The light then passes through one prism of the second polarizing beam splitter 712 and reflects from the hypotenuse surface 713 of the second polarizing beam splitter 712. The light from the second objective lens 722 then passes through the first relay optical system 710 and exits the housing 701. The light then passes through one prism of the first polarizing beam splitter 706 and reflects from the hypotenuse surface 707 towards the camera 102. The camera 102 samples the reflected light. The image processor/controller processes the sampled images to produce a second video stream for display to the user. The second video stream may be displayed simultaneously with the first video stream to produce a stereo image. Because the reflected light received through the first and second objective lenses 718 and 722 is linearly polarized in different directions when passing through the laparoscope, the light can exist at the same axial location inside the laparoscopic housing 701. In other words, the laparoscope 700 includes a shared optical path for multiple reflected light signals when used in stereo mode. As a result, the housing of the laparoscope can be made smaller and the number and size of the incisions in the patient are reduced.

The present invention is not limited to the laparoscope 700 illustrated in FIG. 7. For example, additional polarizers may be included to increase contrast between reflected light received through the objective lens 718 and the light received through the objective lens 722. The additional polarizers may be included inside the laparoscope 700, inside the camera 100a, inside the camera 102, between the laparoscope 700 and the camera 100a, and/or between the laparoscope 700 and the camera 102. Any arrangement of polarizers that polarizes the reflected light received through the objective lenses 718 and 722 in different directions is within the scope of the invention.

Alternative Embodiments of the Invention Including a Shared Optical Path

The arrangement of polarizers, lenses, and beam splitters that create a shared optical path are not limited to the laparoscopic environment illustrated in FIG. 7. For example, in an alternative embodiment, this arrangement or an equivalent arrangement may be used to provide a shared optical path in any multi-signal optical system. Exemplary optical systems in which a shared optical path according to the invention may be utilized include stereo periscopes, multi-projector systems, or any other optical system having multiple optical signals.

In addition, the arrangement of polarizers, beam splitters, and lenses illustrated in FIG. 7 may be rotated or twisted to scan areas in a panoramic or circular form to gather three-dimensional depth images. For example, the housing 701 may include or be connected to a rotating or twisting member to rotate the objective lenses 712 and 718 to scan a circular or panoramic area. The rotating or twisting member may be a rotating table on which the housing rests or any other structure capable of turning the housing to obtain the desired images. One or more cameras may sample the images received during the scanning. The images recorded by the camera or cameras may be used to gather depth without performing structured light depth extraction. Alternatively, structured light depth extraction may be used to enhance depth in the sampled images.

Augmented Reality Visualization System Including Real-Time Structured Light Depth Extraction System As described above, one application for real-time structured light depth extraction is endoscopic surgery, such as laparoscopic surgery. In this application, structured light depth extraction may be used to produce real-time depth images of the interior of a patient's body. The real-time depth images of the interior of the patient's body may be presented to a user, such as a surgeon, using an augmented reality visualization system. An augmented reality visualization system simultaneously displays images of real objects, such as the interior of a patient's body, with synthetic images of non-existing or non-visible real-world objects generated by a computer. The merging of real and synthetic images may be used to enhance the presentation to the viewer, as will be discussed in more detail below.

Figure 8:
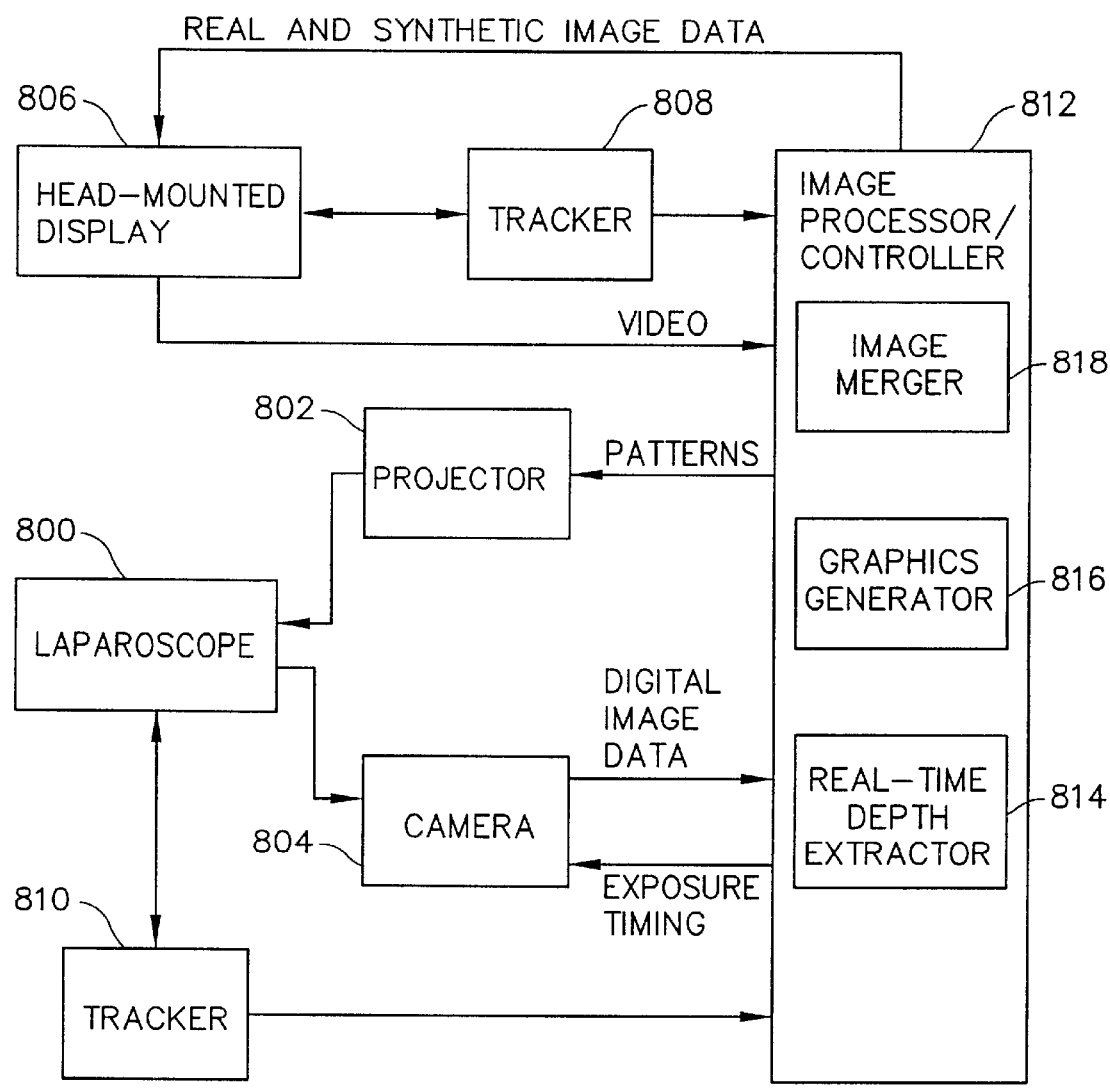
FIG. 8 is a block diagram of an augmented reality visualization system including a real-time structured light depth extraction system according to an embodiment of the present invention.

FIG. 8 is a block diagram of an augmented reality visualization system for laparoscopic surgery including a real-time structured light depth extraction system according to an embodiment of the present invention. In the illustrated embodiment, the visualization system includes a laparoscope 800 for viewing the interior of a patient's body. The laparoscope 800 may be any of the laparoscopes previously described. For example, the laparoscope may be a single laparoscope with a shared optical path as described with respect to FIG. 7. Alternatively, separate laparoscopes may be used for image projection and sampling, as described with respect to FIG. 6.

In order to extract depth and information relating to the interior of the patient's body, the system may include a projector 802 and a camera 804. The projector 802 and the camera 804 are preferably capable of high speed image projection and sampling. The projector 802 and the camera 804 may be the same as or similar to any of the cameras and projectors previously described.

In order to display the three-dimensional image of the interior of the patient to the viewer, the illustrated system includes a head-mounted display 806. The head-mounted display 806 may be any type of display capable of displaying real and synthetic images to the user. For example, the head-mounted display 806 may comprise a video-see-through (VST) head-mounted display or an optical-see-through (OST) head-mounted display. A VST display includes one or more video cameras for acquiring video information of the viewer's surroundings from the viewer's point of view. For example, if the viewer is a surgeon, the video cameras may acquire video images of the operating room and the exterior of the patient's body. The video information detected by the cameras is then merged with the image of the interior of the patient's body and any synthetic images. The merged images are displayed on one or more display screens positioned in front of the viewer's eyes. In a preferred embodiment, the head-mounted display 806 includes two video cameras and two displays for displaying stereo images to the viewer.

Figure 9:
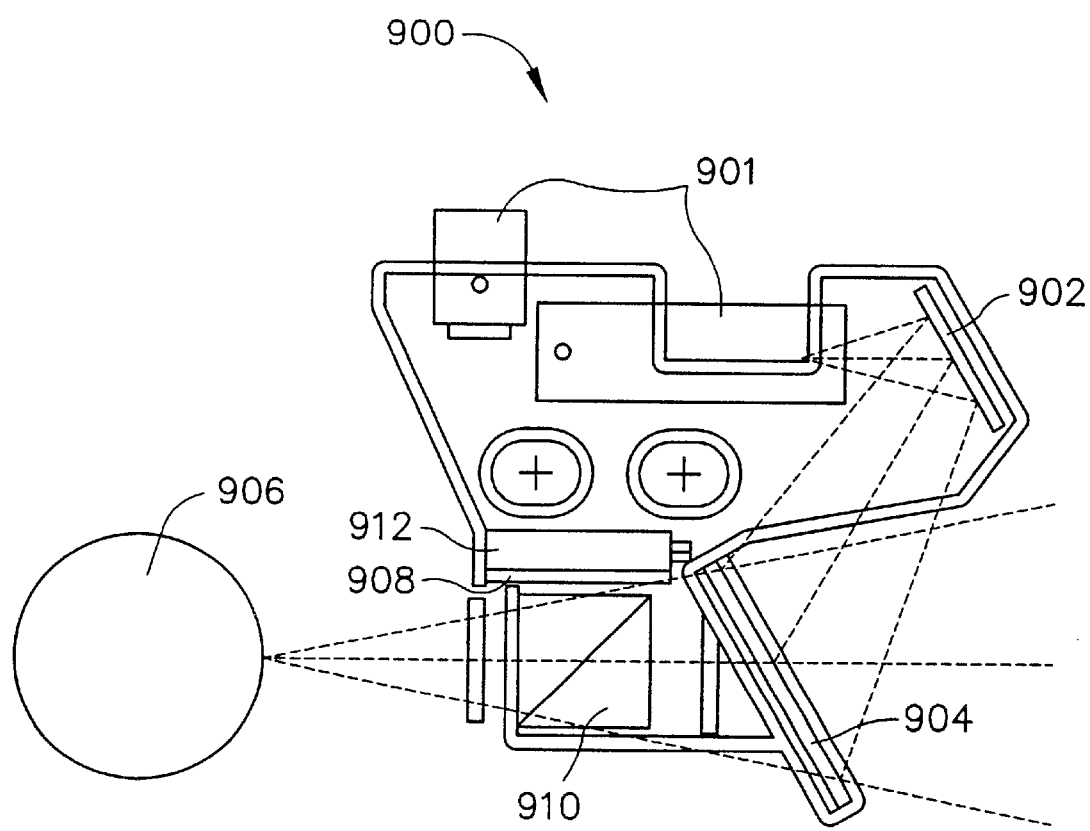
FIG. 9 is an optical schematic diagram of an eyepiece of a head-mounted display used in the augmented reality visualization system of FIG. 8.

FIG. 9 is an optical schematic diagram of one eyepiece 900 of an exemplary VST head-mounted display 806 suitable for use with the present embodiment. In the illustrated embodiment, a video camera 901 gathers video of the external surroundings. First and second mirrors 902 and 904 place the apparent centroid of the camera in the same position as the centroid of a viewer's eye 906 when the head-mounted display 806 is properly mounted to the user's head. A liquid crystal display 908 displays the merged video, depth, and synthetic images to the viewer. A prism assembly 910 folds the optical path multiple times to compress the optical distance between the LCD 908 and the user's eye. A back light 912 provides background lighting for the display 908.

The head-mounted display 806 includes a second eyepiece (not shown), preferably identical to the eyepiece 900 to display stereo images to the viewer. Both of the eyepieces are preferably adjustable to provide one degree of translational freedom and one degree of rotational freedom. This allows the use to adjust the camera distance and the convergence angle. The horizontal bar is preferably hingedly attached to an assembly for mounting the VST head-mounted display 806 to the viewer's head, so that both eyepieces can be flipped up to allow the user to view the word without the assistance of the video cameras.

Referring back to FIG. 8, in order to determine the proper point of view to display an image to the viewer, the system may include a first tracker 808 for tracking the position and orientation of the head-mounted display 806 and thus to some degree, the position and orientation of the viewer's head. Such a tracker preferably includes a high position and orientation update rate, a high degree of accuracy, and a wide range of head positions and orientations. An exemplary tracker that may be used for the tracker 808 is an optical tracker that tracks the position and orientation of the head-mounted display with respect to a ceiling-mounted fixed reference frame.

The system preferably also includes a second tracker 810 for tracking the position and orientation of the laparoscope 800. Tracking the position and orientation of the laparoscope 800 enables proper synthesis of images of the interior of the patient's body. Like the tracker 808, the tracker 810 is preferably accurate and has a high position and orientation update rate. However, the tracker 808 need not have as wide of a range of motion as the tracker 810, since the laparoscope 800 does not move as much as the surgeon's head. An exemplary tracker suitable for tracking the laparoscope is the "FlashPoint" 5000 optical tracker available from Image-Guided Technologies, Inc. The present invention is not limited to an augmented reality visualization system including two tracking systems. Additional tracking systems may be included to track other objects, such as surgical instruments. An image processor/controller 812 includes a real-time depth extractor 814, a graphics generator 816, and an image merger 818. Each of the real-time depth extractor 812, the graphics generator 816, and the image merger 818 may be implemented in hardware, software, or a combination of hardware and software. The real-time depth extractor 812 performs pixel classification and real-time depth extraction to generate three-dimensional depth images of the interior of the patient's body, as previously described. The graphics generator 816 generates synthetic images to be merged with the three-dimensional images. The image merger 818 processes the video signals from the head-mounted display 806, the trackers 808 and 810, merges the three-dimensional images, the video streams, and the synthetic images, and outputs the merged image to the head-mounted display for output to the viewer.

Since the head-mounted display 806 is preferably a video-see-through head mounted display, the image processor/controller 812 is preferably capable of receiving multiple real-time video streams from the cameras of the head mounted display and outputting multiple video signals to the head mounted display. An Onyx2 Infinite Reality system available from Silicon Graphics Inc. equipped with DIVO Video Capture Units may be used to acquire and process the video data, perform the calculations required for depth extraction, and merge the images with the proper occlusion relationships. Alternatively, one or more Matrox Genesis image processors as described with respect to FIG. 1 may be used.

Figures 10A, 10B:
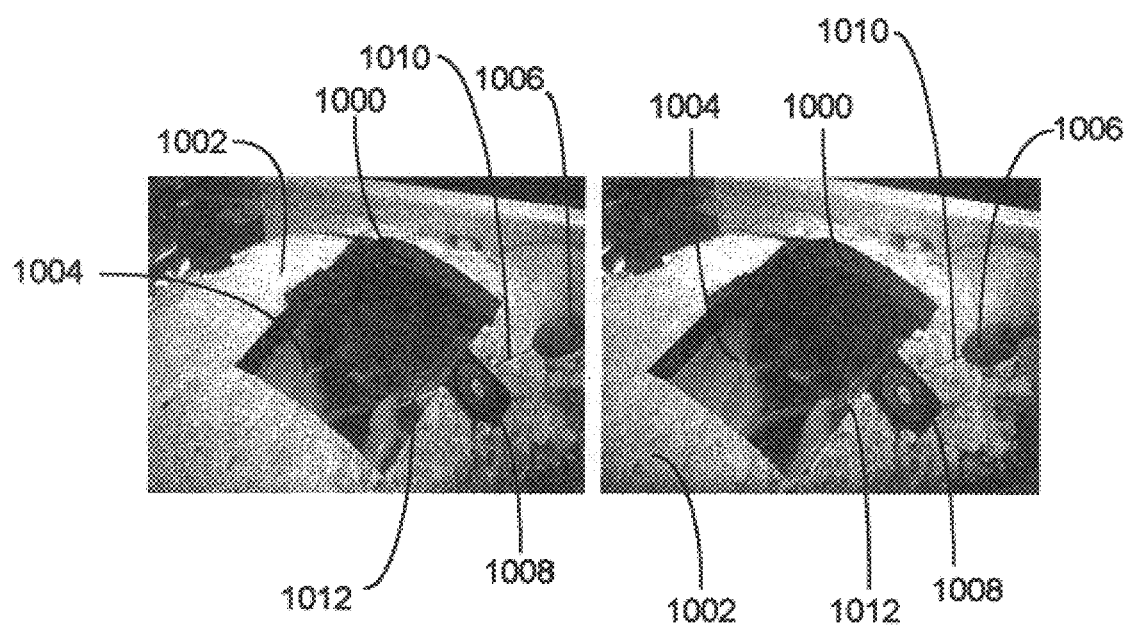
FIGS. 10(a) and 10(b) are a stereoscopic pair of merged real and synthetic images generated by the augmented reality visualization system illustrated in FIG. 8.

As stated above, the graphics generator 816 preferably generates synthetic images for display along with the video and depth images. The synthetic images may be any images used to facilitate laparoscopic surgery. For example, in one embodiment, the synthetic image may comprise a virtual pit representing a viewing window into the patient's body, even though no such pit or hole actually exists. FIGS. 10(*a*) and 10(*b*) illustrate a pair of virtual images that may be seen through the head-mounted display 806. In the illustrated embodiment, a computer graphic of a virtual pit 1000 is superimposed on an image 1002 of the skin of an anatomical model of a patient. A real-time three-dimensional image 1004 of the inside of the patient's body is shown inside the virtual pit 1000. The image 1004 is preferably updated when the patient moves or when the head mounted display moves to change the viewing angle. Thus, a surgeon is no longer required to rely on video images that do not correspond to the direction that the surgeon is facing.

Because the system illustrated in FIG. 8 is capable of extracting depth and updating the image 1004 in real-time, changes in the image 1004 appear continuous to a human observer. An image 1006 of a needle is also shown piercing a target 1008 in the image 1002 of the model's skin. The image 1006 of the needle includes a first portion 1010 that is outside the patient's body and a second portion 1012 that is inside the patient's body. The first portion 1010 is a real image acquired by the video cameras of the head-mounted display 806. The second portion 1012 is synthetic and may be generated from a tracker and the geometry of the needle. In order to display the correct relationship between the synthetic portion of the needle and the interior of the patient's body the image processor/controller preferably compares depth values extracted using the laparoscopic camera with the signals from the needle tracking system. For example, if the needle penetrates a surface within the interior of the patient's body, the synthetic portion 1012 of the displayed image of the needle should be occluded by the surface that it penetrates. Because the real-time structured light depth extraction system is capable of accurately determining depth, the correct relationship is displayed. Thus, the combination of augmented reality visualization with real-time structured light depth extraction greatly enhances endoscopic surgery.

It will be understood that various details of the invention may be changed without departing from the scope of the invention. Furthermore, the foregoing description is for the purpose of illustration only, and not for the purpose of limitation--the invention being defined by the claims.

What is claimed is:

1. A real-time structured light depth extraction system for producing real-time images in an endoscopic surgical environment comprising:

(a) a projector for projecting structured light patterns onto an object inside of a patient's body, each structured light pattern including a plurality of pixels being simultaneously projected onto the object;

(b) at least one endoscope optically coupled to the projector for communicating the structured light patterns from the projector to a first region inside of the patient's body and for communicating reflected structured light patterns from the first region to a second region outside of the patient's body;

(c) a camera optically coupled to the endoscope for sampling the reflected light patterns and outputting digital signals indicative of the reflected light patterns; and (d) an image processor/controller coupled to the camera to receive the digital signals and extract depth information of the object in real time.

2. The real-time structured light depth extraction system of claim 1 wherein the endoscope comprises a single endoscope having a shared optical path for communicating the structured light patterns from the projector to the first region and for communicating the reflected light patterns from the first region to the camera.

3. The real-time structured light depth extraction system of claim 2 wherein the single endoscope comprises a laparoscope.

4. A real-time structured light depth extraction system for producing real-time images in an endoscopic surgical environment comprising:

(a) a projector for projecting structured light patterns onto an object inside of a patient's body;

(b) at least one endoscope optically coupled to the projector for communicating the structured light patterns from the projector to a first region inside of the patient's body and for communicating reflected structured light patterns from the first region to a second region outside of the patient's body;

(c) a camera optically coupled to the endoscope for sampling the reflected light patterns and outputting digital signals indicative of the reflected light patterns; and (d) an image processor/controller coupled to the camera to receive the digital signals and extract depth information of the object in real time, wherein the endoscope comprises a first endoscope for communicating the structured light patterns from the projector to the first region and a second endoscope for communicating the reflected light patterns from the first region to the camera.

5. The real-time structured light depth extraction system of claim 4 wherein the first and second endoscopes comprise first and second laparoscopes.

6. An augmented reality visualization system for endoscopic surgery comprising:

(a) at least one endoscope for viewing objects inside of a patient's body;

(b) a real-time structured light depth extraction system coupled to the endoscope for projecting structured light patterns into the patient's body, receiving light reflected from the objects, determining depth information relating to the objects in real time, and producing three-dimensional images of the objects;

(c) a graphics generator for generating synthetic images;

(d) an image merger for merging the three-dimensional images and the synthetic images to produce merged images having correct occlusion relationships; and (e) a display for displaying the merged images to a viewer.

7. The augmented reality visualization system of claim 6 wherein the display comprises a head-mounted display.

8. The augmented reality visualization system of claim 6 wherein the display comprises an optical-see-through (OST) head-mounted display.

9. The augmented reality visualization system of claim 6 wherein the display comprises a video-see-through (VST) head-mounted display including first and second video cameras for producing first and second video streams indicative of the viewer's surroundings.

10. The augmented reality visualization system of claim 9 comprising a first tracker for tracking position and orientation of the endoscope and outputting a first tracking signal based on the position and orientation of the endoscope and a second tracker for tracking position and orientation of the viewer's head and outputting a second tracking signal based on the position and orientation of the viewer's head, wherein the image merger merges the first and second video streams, the three-dimensional images, and the synthetic images to produce the merged images based on the depth information and the first and second tracking signals.

11. The augmented reality visualization system of claim 6 wherein the real-time structured light depth extraction system comprises:

(a) a projector optically coupled to the endoscope for projecting, from a first position, structured light patterns into the patient's body;

(b) a camera optically coupled to the endoscope for receiving, from a second position, light reflected from the objects inside of the patient's body synchronously with projection of the structured light patterns; and (c) a depth extractor for calculating depth information relating to the objects inside of the patient's body based on the structured light patterns, the light received by the camera, and the first and second positions.

12. The augmented reality visualization system of claim 6 wherein the endoscope comprises a single endoscope having a shared optical path for transmitting structured light patterns into the patient's body and receiving light reflected from the objects inside of the patient's body.

13. The augmented reality visualization system of claim 11 wherein the single endoscope comprises a single laparoscope.

14. The augmented reality visualization system of claim 6 wherein the endoscope comprises a first endoscope for communicating structured light patterns into the patient's body and a second endoscope for receiving light reflected from the objects inside of the patient's body.

15. The augmented reality visualization system of claim 14 wherein the first and second endoscopes comprise first and second laparoscopes.

* * * * *